United States Patent [19]

Plumley

[11] 4,270,542
[45] Jun. 2, 1981

[54] GASTRO-INTESTINAL TUBES

[76] Inventor: Peter F. Plumley, 8 Wealden Way, Bexhill, Sussex, England

[21] Appl. No.: 81,242

[22] Filed: Oct. 2, 1979

[30] Foreign Application Priority Data

Oct. 9, 1978 [GB] United Kingdom ............... 39848/78

[51] Int. Cl.³ ........................................... A61M 27/00
[52] U.S. Cl. ................................................. 128/350 R
[58] Field of Search .............. 128/350 R, 240, 349 R, 128/349 B, 348

[56] References Cited

U.S. PATENT DOCUMENTS

| | | | |
|---|---|---|---|
| 1,899,781 | 2/1933 | Twiss | 128/350 R |
| 2,492,384 | 12/1949 | Kaslow | 128/350 R |
| 3,114,373 | 12/1963 | Andersen | 128/350 R |
| 3,395,710 | 8/1968 | Stratton et al. | 128/350 R |
| 3,495,595 | 2/1970 | Soper | 128/350 R |
| 3,528,427 | 9/1970 | Sheridan et al. | 128/240 X |
| 3,726,283 | 4/1973 | Dye et al. | 128/350 R |
| 3,788,328 | 1/1974 | Alley et al. | 128/350 R |
| 4,119,100 | 10/1978 | Rickett | 128/349 B |

Primary Examiner—John D. Yasko
Attorney, Agent, or Firm—Pollock, Vande Sande & Priddy

[57] ABSTRACT

A naso-gastric tube has a large bore through which gas and liquid can be removed from the stomach and oesophagus, and a small bore through which liquid can be introduced to the duodenum. The large bore is closed at one end of the tube whereas the small bore opens at this end. The tube has a region of several apertures through which the large bore opens from the tube; the region is spaced from the end of the tube by a first distance of at least 10 cm, the region extending for a second distance approximately equal to the first distance. In this way, when the open end of the small bore is located in the duodenum, the apertures will be located in the lower oesophagus and the upper part of the stomach.

9 Claims, 3 Drawing Figures

GASTRO-INTESTINAL TUBES

BACKGROUND OF THE INVENTION

This invention relates to gastro-intestinal tubes.

The invention is particularly concerned with gastro-intestinal tubes having provision both for enabling fluid to be supplied to the pylorus or duodenum and also for enabling simultaneous aspiration of gas or liquid from the stomach.

Such tubes are commonly used, for example, following surgery, to supply feeding fluid, such as dextrose solution, or medicaments directly to the small intestine. Previously used tubes generally comprise a large-bore tube which is sealed at one end, and a small-bore tube extending along the outside of the large-bore tube. The small-bore tube extends beyond the end of the large-bore tube by a sufficient distance to enable it to reach the duodenum when the large-bore tube is situated in the stomach. Feeding liquid can be supplied to the small intestine through the small-bore tube while liquid or gas at the bottom of the stomach can be withdrawn through the large-bore tube via a number of apertures in its wall in the region of the closed end.

It is desirable in many circumstances, however, to remove fluid from the oesophagus as well as from the stomach, such as, for example, to prevent entry of swallowed fluid into the stomach. While previous tubes can be used fairly satisfactorily to remove fluid from the bottom of the stomach it is extremely difficult to introduce and position them so that fluid can be removed from both the stomach and oesophagus, while at the same time maintaining the end of the small-bore tube in its correct position in the region of the duodenum.

SUMMARY OF THE INVENTION

It is an object of the present invention to provide a gastro-intestinal tube that can be used to alleviate the above-mentioned difficulties.

According to one aspect of the present invention there is provided a gastro-intestinal tube having a first bore for enabling fluid to be removed from the stomach and oesophagus of a patient, the first bore extending to, and being closed at, one end of the tube; a multiplicity of apertures in the wall of the tube through which said first bore opens, the apertures being spaced apart from one another over a region along the length of the tube, said region being spaced from said one end of said tube by a first distance of at least 10 cm and extending for a second distance at least substantially equal to said first distance; and a second bore for enabling fluid to be supplied to the duodenum of the patient, the second bore extending to, and opening at, said one end of the tube such that, when the tube is located with said one end in the region of the duodenum, some of said apertures are located in a lower part of the oesophagus and others of said apertures are located in an upper part of the stomach.

Gastro-intestinal tubes in accordance with the present invention can be used effectively to remove fluid from the upper region of the stomach and the lower region of the oesophagus. In this way, by aspirating from the oesophagus, swallowed liquid and gas can be prevented from entering the stomach, while a liquid nutriment or medicament can be supplied to the duodenum.

A naso-gastric tube in accordance with the present invention, will now be described, by way of example, with reference to the accompanying drawings.

DETAILED DESCRIPTION

Figure 1:
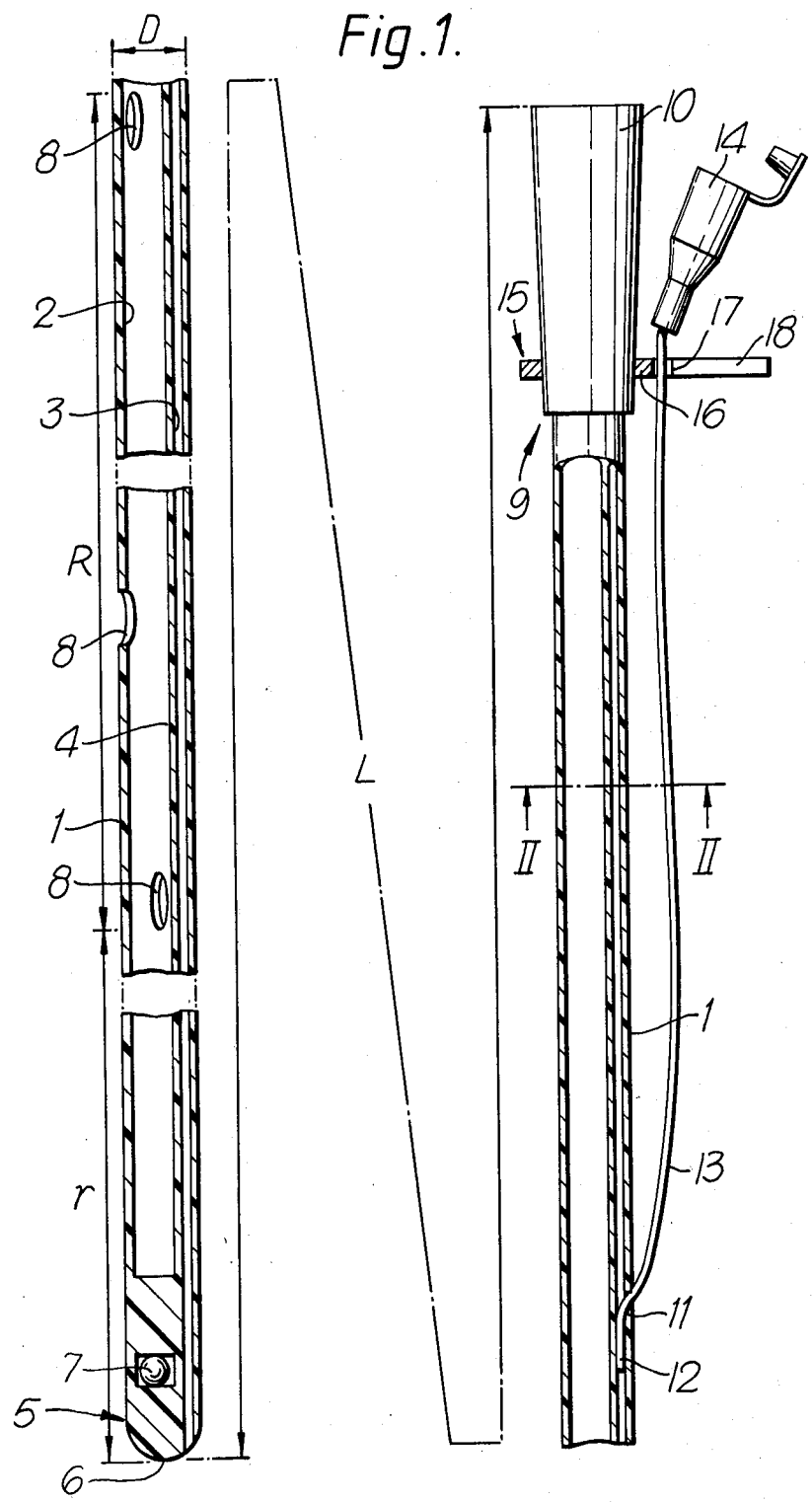
FIG. 1 is a fragmentary cross-section of the naso-gastric tube.
Figure 2:
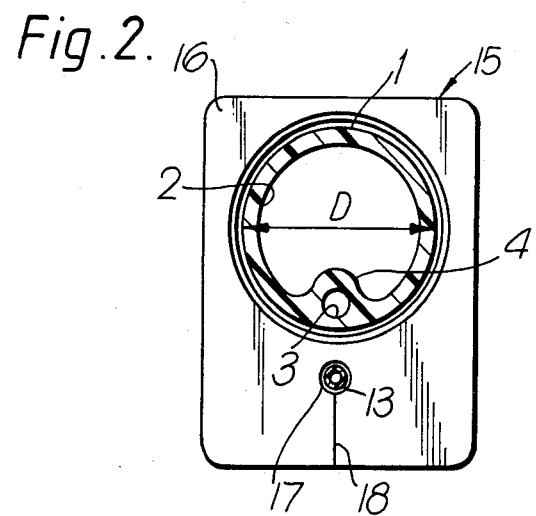
FIG. 2 is an enlarged sectional view across the diameter of the tube, taken on the line II—II of FIG. 1.

With reference to FIGS. 1 and 2, the naso-gastric tube comprises an extruded length of PVC tubing 1 having a large diameter bore 2 extending along its length, and a smaller diameter bore or lumen 3 extending through the wall of the tubing 1 along its length. The tube has a smooth, circular outer surface, the small diameter lumen 3 extending through a ridge 4 projecting on the inner surface of the wall of the tube.

The patient end 5 (that is, the end of the tube which is to be located within the patient) of the large-diameter bore 2 is sealed by melting the end of the tubing 1 so as to form a rounded tip 6 in which is embedded a steel ball 7. The ball 7 provides a radio-opaque marker for determining the location of the tip during use and also adds weight to the tip to assist in positioning the tube. A series of about twenty apertures 8 (only three of which are shown in FIG. 1) are formed in the wall of the tube, the first aperture being spaced from the tip 6 by a distance r of about 20 cm. The apertures are spaced apart from one another in a helical fashion about the tube, in a region which extends over a distance R, also of about 20 cm.

The other, machine end 9 of the tube has an adaptor 10 sealed to it which serves to make connection to a suction pump (not shown). The entire length L of the tube, from its tip 6 to the machine end 9 of the adaptor 10 is about 145 cm.

The small-diameter lumen 3 extends the entire length of the tubing 1, from the patient end 5 to the adaptor 10 at the machine end 9 of the tube. The lumen 3 is open at the patient end 5 but is closed at the machine end 9 of the tube. Connection to the small-diameter lumen 3 is made through an opening 11 in the wall of the tubing 1 by one end 12 of a small-bore flexible tube or conduit 13. The end 12 of the small-bore tube 13 is inserted a short distance within the lumen 3 towards the patient end 5 and is secured in position by means of a solvent applied to the outer surface of the end of small-bore tube. The small-bore tube 13 is terminated with a Luer connector 14 that can be used to make connection with a fluid-supply container (not shown).

A retaining clip 15 is mounted on the adaptor 10 and comprises a plate 16 of flexible PVC having an aperture 17 for receiving the small-bore tube 13. The plate 16 has a cut 18 extending from the aperture 17 to one edge, thereby enabling the small-bore tube 13 to be readily inserted and removed from the clip. The clip 15 is used to keep the small-bore tube 13 and its Luer connector 14 close to the adaptor 10 during placement of the tube and thereby reduce the risk that the small-bore tube 13 might catch on clothing or equipment and strain the joint with the lumen 3.

Figure 3:
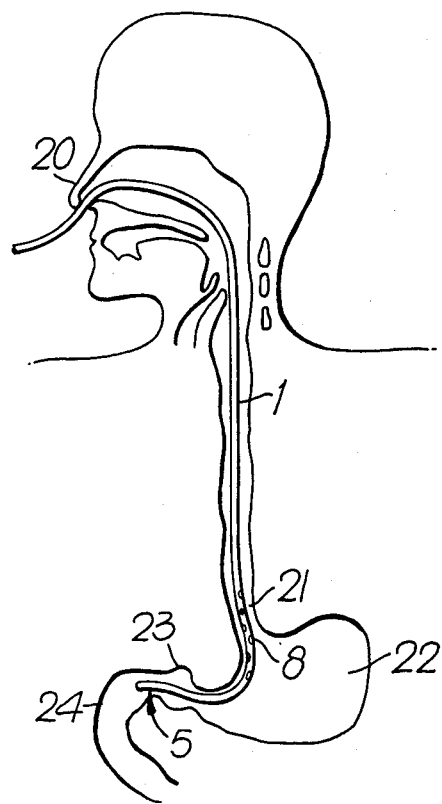
FIG. 3 shows the tube in use.

With reference to FIG. 3, the tube is, in use, passed through the nose 20 of a patient, down his oesophagus 21 and through the body of his stomach 22 and pylorus 23 such that the patient end 5 of the tube projects into his duodenum 24. Feeding liquid may, therefore, be supplied directly to the duodenum 24 via the small-bore lumen 3, which opens at the patient end 5. The length r, by which the apertures 8 are spaced from the patient end 5 of the tube, and the length R over which the apertures are disposed are such that, with the patient end 5 projecting into the duodenum as shown, the apertures are distributed approximately equally in the upper region of the stomach 22 and in the region of the oesophagus 21 close to the stomach. In this way, when suction is applied (by connecting the large-bore 2 at the machine end 9 of the tube to a suitable pump) gas is readily removed from the stomach and oesophagus and any distension is rapidly alleviated.

Introduction and correct placement of the tube within the stomach may be assisted by inserting a stilette, that is, a metal strip-shape spring element, into the large-diameter bore 2 so as to provide a greater degree of resilience to the tube, the stilette being removed when the tube is correctly positioned. Alternatively, the stilette could be in the form of a flexible rod of plastics material which is inserted within the large-diameter bore 2 to render the tube as a whole less flexible. In a tube of alternative construction the stilette could be inserted within the smaller-diameter bore 3.

It will be understood that the tube may be modified by, for example, using a different number of apertures, and may be made in a range of different sizes for use by different patients from children to adults. In particular, the outside diameter D of the tube may be between about 10 and 20 f.g. (french gauge—3 f.g. is equal to 1 mm); the length r may be between about 10 cm and 25 cm; and the length R between about 10 cm and 30 cm. The two lengths r and R should be approximately equal, although they need not be exactly equal as can be seen for the largest tube, where r and R are 25 cm and 30 cm respectively.

It would alternatively be possible to have a small-diameter tube extending along the outside wall of the tubing instead of within its wall.

I claim:

1. A gastro-intestinal tube having: a first bore for enabling fluid to be removed from the stomach and oesophagus of a patient, said first bore extending to, and being closed at, one end of said tube; a multiplicity of apertures in the wall of said tube through which said first bore opens, said apertures being spaced apart from one another over a region along the length of said tube, the first aperture in said region being spaced from said one end of said tube by a first distance of at least 10 cm and said region extending for a second distance substantially equal to said first distance; and a second bore for enabling fluid to be supplied to the duodenum of the patient, said second bore extending to, and opening at, the said one end of said tube such that when said tube is located with its said one end in the region of the duodenum some of said apertures are located in a lower part of the oesophagus and others of said apertures are located in an upper part of the stomach.

2. A gastro-intestinal tube according to claim 1, wherein said second bore has a smaller cross-sectional area than said first bore, and wherein said second bore extends through the wall along the length of said tube.

3. A gastro-intestinal tube according to claim 1, wherein said tube has a mass located at said one end so as thereby to increase the weight of said one end.

4. A gastro-intestinal tube according to claim 3, wherein said mass is a metal ball embedded in said tube.

5. A gastro-intestinal tube according to claim 1, wherein said apertures are spaced around the circumference of said tube.

6. A gastro-intestinal tube according to any one of claims 1 to 5, wherein said tube is of plastic material.

7. A gastro-intestinal tube according to claim 6, wherein said tube is of PVC.

8. A gastro-intestinal tube according to any one of claims 1 to 5, including a flexible conduit, said conduit having one end connected with said second bore.

9. A gastro-intestinal tube according to claim 8, including retaining means mounted with said tube, said retaining means defining an aperture within which said conduit can be retained.

* * * * *